United States Patent
Fattori Martegani

(10) Patent No.: US 9,517,848 B2
(45) Date of Patent: Dec. 13, 2016

(54) DIRECT BROADCAST ALERT APPARATUS AND METHOD

(71) Applicant: AVIOSONIC SPACE TECH Srls, Milan (IT)

(72) Inventor: Piermarco Fattori Martegani, Milan (IT)

(73) Assignee: AVIOSONIC SPACE TECH SRLS, Milan (IT)

( * ) Notice: Subject to any disclaimer, the term of this patent is extended or adjusted under 35 U.S.C. 154(b) by 0 days.

(21) Appl. No.: 14/418,496

(22) PCT Filed: Jul. 31, 2013

(86) PCT No.: PCT/IB2013/056295
§ 371 (c)(1),
(2) Date: Jan. 30, 2015

(87) PCT Pub. No.: WO2014/020556
PCT Pub. Date: Feb. 6, 2014

(65) Prior Publication Data
US 2015/0203218 A1 Jul. 23, 2015

(30) Foreign Application Priority Data
Aug. 1, 2012 (IT) .............................. MI2012A1352

(51) Int. Cl.
*G08B 21/00* (2006.01)
*B64G 1/56* (2006.01)
(Continued)

(52) U.S. Cl.
CPC . *B64G 1/56* (2013.01); *B64G 3/00* (2013.01); *G01M 5/0033* (2013.01);
(Continued)

(58) Field of Classification Search
CPC ........... B64G 1/242; B64G 1/62; B64G 1/007; G01M 5/0033; G01N 2291/2694
(Continued)

(56) References Cited

U.S. PATENT DOCUMENTS 8,060,319 B2* 11/2011 Stothers ............... G01N 29/045
702/39
9,180,632 B2* 11/2015 Hemmelgarn ...... B29C 35/0272
(Continued)

FOREIGN PATENT DOCUMENTS

JP 5278698 10/1993

OTHER PUBLICATIONS

Anselmo, L., et al., "Computational Methods for Reentry Trajectories and Risk Assessments", Advances in Space Research, Pergamon, Oxford, GB, vol. 35, No. 7, Jan. 1, 2005, pp. 1343-1352.
(Continued)

*Primary Examiner* — John A Tweel, Jr.
(74) *Attorney, Agent, or Firm* — Silvia Salvadori, P.C.; Silvia Salvadori

(57) ABSTRACT

An alert apparatus and an alert method implemented by said direct broadcast apparatus for protection against collisions with debris and the like found in the Earth's atmosphere or in space, said apparatus comprising: —a containing structure mounted outside or inside a body of an aircraft, of a space vehicle or of a flying object in general which moves through the atmosphere or the space, in which sensor means are housed that is arranged for checking a release of debris and the like, coming from said body following an explosion and/or ablation thereof that are dispersed in a hazard space (2) and/or arranged for checking conditions that are referable to said explosion and/or ablation and for detecting features of the hazard space (2), —a processing unit, arranged in the containing structure, connected to the sensor
(Continued)

means for processing the features of the hazard space (2) in order to determine the extent and the dynamics of the hazard space (2); —transceiver means arranged for sending an output signal (B) carrying an alert message on the basis of the extent and of the dynamics of said hazard space (2) to a space vehicle (3) and/or to an aircraft (4) having a route intersecting the hazard space (2), and/or to a ground station (5, 17) and/or to an end user (6, 16) arranged on the Earth's surface (20) at a presumed impact area between the hazard space (2) and the Earth's surface (20) in order to activate respective emergency procedures, the sensor means and the transceiver means being positioned at the hazard space.

12 Claims, 3 Drawing Sheets

(51) Int. Cl.
  *G01M 5/00* (2006.01)
  *G08G 5/00* (2006.01)
  *B64G 3/00* (2006.01)
  *G08G 5/04* (2006.01)

(52) U.S. Cl.
  CPC ......... *G08G 5/0008* (2013.01); *G08G 5/0013* (2013.01); *G08G 5/04* (2013.01); *G01N 2291/2694* (2013.01)

(58) Field of Classification Search
  USPC .............. 340/963, 945; 324/240; 244/158.1; 701/301, 302
  See application file for complete search history.

(56) References Cited

U.S. PATENT DOCUMENTS

| | | | |
|---|---|---|---|
| 2004/0024527 A1 | 2/2004 | Patera | |
| 2004/0254697 A1* | 12/2004 | Ailor | B64G 1/62 701/32.2 |
| 2007/0285304 A1* | 12/2007 | Cooper | B64G 1/007 342/62 |
| 2013/0082146 A1* | 4/2013 | Kofford | B64G 4/00 244/158.7 |
| 2014/0232599 A1* | 8/2014 | Behrens | G01S 13/06 342/385 |
| 2015/0331080 A1* | 11/2015 | Sgobba | G08B 21/02 340/539.1 |
| 2015/0338306 A1* | 11/2015 | Dunne | G01M 5/0033 73/587 |

OTHER PUBLICATIONS

Search Report and Written Opinion of corresponding PCT/IB2013/056295 of Nov. 12, 2013.

* cited by examiner

DIRECT BROADCAST ALERT APPARATUS AND METHOD

This application is a U.S. national stage of PCT/IB2013/056295 filed on 31 Jul. 2013, which claims priority to and the benefit of Italian Application No. MI2012A001352, filed on 1 Aug. 2012, the contents of which are incorporated herein by reference in their entirety.

The invention relates to an alert apparatus for the safety of aircraft or space vehicles in flight or for the safety of things or people on the Earth's surface, in particular for protection against collisions with debris and the like present in the Earth's atmosphere.

The alert apparatus according to the invention is arranged for detecting and transmitting information on a space of the Earth's atmosphere considered to be a hazard for the route of aircraft, space vehicles or flying space objects in general or for things or persons on the Earth's surface inasmuch as inside the space there may be debris, gas and/or chemical solutions coming from another aircraft or space vehicle, following the explosion or ablation thereof or another event that causes fragmentation thereof, and which can collide with such aircraft or space vehicles in flight or things or persons on the Earth's surface, impairing the safety thereof.

In fact, any aircraft, space vehicle or flying object in general that moves through the atmosphere or space comprises a casing provided with an external surface arranged in contact with the air of the Earth's atmosphere which, during the descent or ascent in the atmosphere, reentry or departure from and for a mission or from a high-altitude flight or suborbital flights, owing to the high temperatures and loads that it has to support, may be subject to partial or total fragmentation that causes the release in the Earth's atmosphere of debris and the like. This partial or total fragmentation can also be caused by either the commanded explosion or the autonomous explosion of pyrotechnical apparatuses.

The debris and the like falling from the atmosphere to the Earth's surface is distributed within a so-called hazard space that may also have significant dimensions and that creates a concrete risk of accidents or disasters.

In fact, whilst such debris descends to the Earth's surface it may hit other aircraft, space vehicles or flying space objects in general, jeopardising things or persons in such objects and generating further debris released from the latter following the impact with the debris of the hazard space.

Further, at the end of the descent from the atmosphere, the debris of the hazard space may impact the Earth's surface, jeopardising also things or persons thereupon.

Recent studies have demonstrated that it is sufficient for a piece of debris falling in the atmosphere weighing more than 300 g to impact an aircraft, a space vehicle or a flying object in general moving through the atmosphere or space for the latter to be destroyed or seriously damaged.

In order to protect persons or things in flight or on the Earth's surface from the impact with potential fragments of aircraft, space vehicles or space objects in general, an alert system is known that is able to send information on the hazard space in which said fragments are dispersed.

This alert system comprises a radar system positioned on the Earth's surface that monitors the atmosphere and detects information on hazard spaces that are possibly present.

The information on the hazard space cannot therefore be broadcast directly and has very high approximation. For example in the case of information on the position of the hazard space, the approximation can also be in the order of thousands of kilometers.

A drawback of such alert systems is that they are not efficient, inasmuch, owing to the less than total global coverage of the air traffic control services there are too many intermediaries in the decision-making chain that are due to current laws and to safety procedures, immediate activation of emergency procedures is not guaranteed that aim to shield or bring out of the hazard space an aircraft, a space vehicle or a flying object in general that moves through the atmosphere or the space the motion trajectory of which is intended to pass through the hazard space. For example, in the case of aircraft, an emergency procedure could take the form of a timely evasive manoeuvre, whereas for the persons on the Earth's surface it would take the form of the immediate search of a shelter.

For sensitive installations, such as for example electric power stations, chemical plants, nuclear power stations or on-land or off-shore drilling rigs, an emergency procedure to avoid the hazard that could arise could consist of making the plant secure and activating alert or emergency procedures.

An object of the invention is to improve prior-art alert apparatuses.

Another object is to obtain an efficient alert apparatus, i.e. an apparatus that is able to ensure coverage of the transmission of information on a hazard space even in zones that are not reached directly by the control services of the air traffic control such as, for example, the routes of transoceanic flights.

A further object is to obtain an alert apparatus that is able to ensure the transmission of current information on the position and features of the hazard space directly from the interior thereof.

According to the invention an alert apparatus is provided as defined in claim 1.

According to the invention an alert method is provided as defined in claim 9.

Owing to the invention, it is possible to obtain a significantly efficient alert apparatus.

The invention can be better understood and implemented with reference to the attached drawings that illustrate embodiments thereof by way of non-limiting example, in which.

Figure 1:
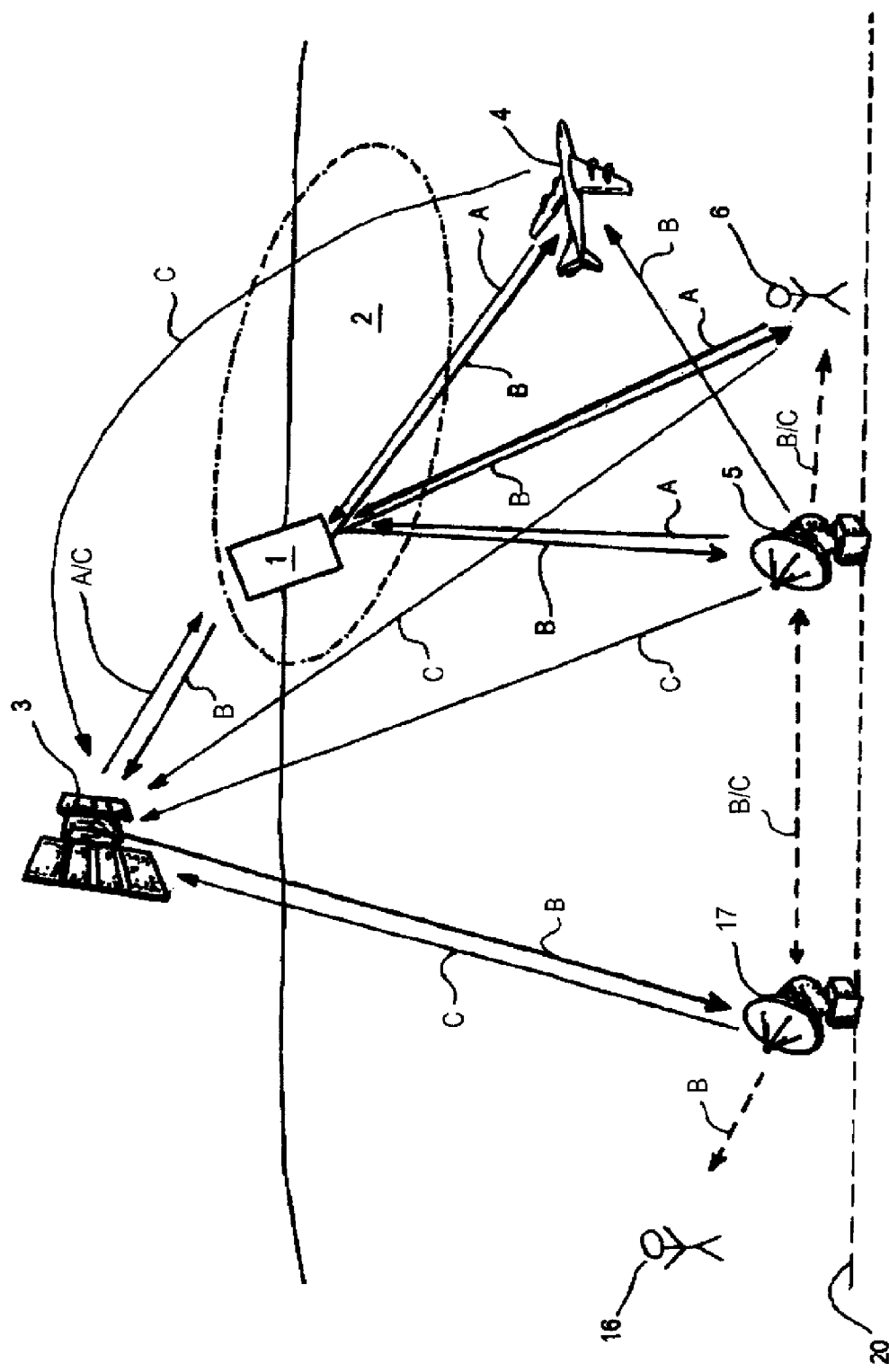
FIG. 1 is a diagram of an alert apparatus according to the invention in communication with interface units to send information on a hazard space.

With reference to FIG. 1, an alert apparatus 1 is illustrated that is suitable for monitoring, detecting, defining and broadcasting data on a hazard space 2 for the safety of aircraft, space vehicles or flying space objects in general or for the safety of things or people on the Earth's surface 20.

In particular, the alert apparatus 1 according to the invention is suitable for warning a user of the possibility of collisions with debris, gas and/or chemical solutions, and the like distributed in the aforesaid hazard space 2.

The Earth's surface 20 is shown in FIG. 1 by a dashed line.

The hazard space 2 is defined by the volume of atmosphere occupied by debris and the like that are generated following an explosion, fragmentation and/or ablation, as will be explained better below, whilst the latter fall from the atmosphere to the Earth's surface 20 and by the area of the Earth's surface on which the debris and the like are distributed when impact the Earth's surface 20.

In FIG. 1, the hazard space 2 is represented enclosed inside a dot-dash line that delineates an ellipse, which represents a two-dimensional projection of the volume occupied by debris and the like.

It is obvious that an ellipse is one of the various flat geometrical figures that the bidimensional projection of the volume occupied in the atmosphere by the debris and the like can adopt.

More in general, the two-dimensional projection of the volume occupied in the atmosphere by the debris and the like can adopt the shape of any regular or irregular geometrical figure.

The alert apparatus 1 is mounted on a surface of a body of a aircraft, space vehicle or flying object in general that moves through the atmosphere or the space, not illustrated in FIG. 1.

In particular, the alert apparatus 1 can be arranged on an internal surface of said body, on an external surface of said body or in general, can be housed inside of said body.

The alert apparatus 1 is provided with a containing structure that is able to withstand heat, mechanical and pressure stress and physical phenomena that are generated during the entire service cycle of the alert apparatus 1 when, in particular, the aircraft, space vehicle or flying object in general that moves through the atmosphere or the space on which it is mounted, traverses the atmosphere and suffers an explosion and/or ablation, following which the alert apparatus 1 activates or is activated.

During descent from or ascent into the atmosphere, owing to the high temperatures and loads that it has to support, the aforesaid containing structure and the external surface of the body of a aircraft, space vehicle or flying object in general that moves through the atmosphere or the space can be subject to an explosion or ablation that causes the release in the Earth's atmosphere of debris, gas and/or chemical solutions.

The release into the Earth's atmosphere of debris, gas and/or chemical solutions can also be caused by either a commanded explosion or an autonomous explosion of an aircraft and/or vehicle and/or space object.

The distribution of this debris and the like in the Earth's atmosphere constitutes, as said, the hazard space 2.

This debris and the like can hit during the descent motion to the Earth's surface 20, another aircraft, space vehicle or flying object in general that moves through the atmosphere or the space, having a route intersecting with the hazard space 2, not only jeopardising things or persons in such objects in flight but also generating further debris and the like released following the impact between the other aircraft, space vehicle or flying object in general that moves through the atmosphere or the space, and the debris of the hazard space 2.

Further, at the end of the descent from the Earth's atmosphere, the debris may impact the Earth's surface 20 jeopardising also things or people present thereupon at the impact area between the hazard space 2 and the Earth's surface 20.

From what has been set out above and from the fact that the hazard space 2 comprises a plurality of debris and the like each having its own descent motion, it emerges that the hazard space 2, defined following an explosion or ablation of the external surface of a body of aircraft, space vehicle or flying object in general that moves through the atmosphere or the space on which the alert apparatus 1 is mounted, evolves with the passing of time from the altitude at which the fragmentation occurred, varying in extent and in composition.

Consequently, in order to protect persons or things in flight or on the Earth's surface 20 that could be hit by the debris and the like, it is necessary to detect directly and promptly real information on the hazard space 2 comprising debris and the like that, from the altitude at which fragmentation occurred, descend to the Earth's surface 20.

As will be seen below, this information comprises a plurality of parameters defining the features of the hazard space 2, including position, altitude, direction and speed.

On the basis of this information on the hazard space 2, the alert apparatus 1 broadcasts one or more alert messages to interface units.

The interface units may comprise a space vehicle 3, such as, for example, an artificial satellite, a space shuttle, a space vehicle or a space station, an aircraft 4, a ground station 5, or a processor of an end user 6.

The alert messages have the objects of warning the interface units of the creation of the hazard space 2 and of the features thereof in such a manner that, for example, an aircraft 4, having the route intersecting the hazard space 2, can perform deviating manoeuvres to avoid or take out of the hazard space 2, a sensitive plant on the land or at sea (such as an electric power station, chemical plant, nuclear power station, a ship or on-land or off-shore drilling rig) arranged at a zone of possible impact of the debris of the hazard space 2 with the Earth's surface 20, can be made safe or a person, also located in a zone of possible impact of the debris of the hazard space 2 with the Earth's surface 20, can find suitable shelter.

The alert apparatus 1 comprises transceiver means arranged for managing and controlling the communication between the alert apparatus 1 and the interface units, each of which is arranged for receiving the alert messages from the alert apparatus 1 and can also be arranged for sending information to the alert apparatus 1.

The transceiver means comprises receiving and transmitting means, respectively designed to receive input signals A from the alert apparatus 1 coming from an interface unit and to transmit output signals B from the alert apparatus 1 to an interface unit.

The input signals A may comprise information and/or commands for running the alert apparatus 1 coming either from a system positioned inside the body of the vehicle on which the alert apparatus 1 is mounted, for example through a wireless connection, or from a system outside the alert apparatus 1.

The information carried by the input signals A comprises amongst other things the position of the alert apparatus 1 in space or the parameters to define the position.

For example, a system outside the alert apparatus 1 can be an artificial constellation of satellites including the GPS, GALILEO or Iridium systems or, as illustrated in FIG. 1, a space vehicle 3.

A system inside the body of the vehicle can be an inertia positioning system that obtains a position of the alert apparatus 1 in space starting form a known initial position.

Figure 2:
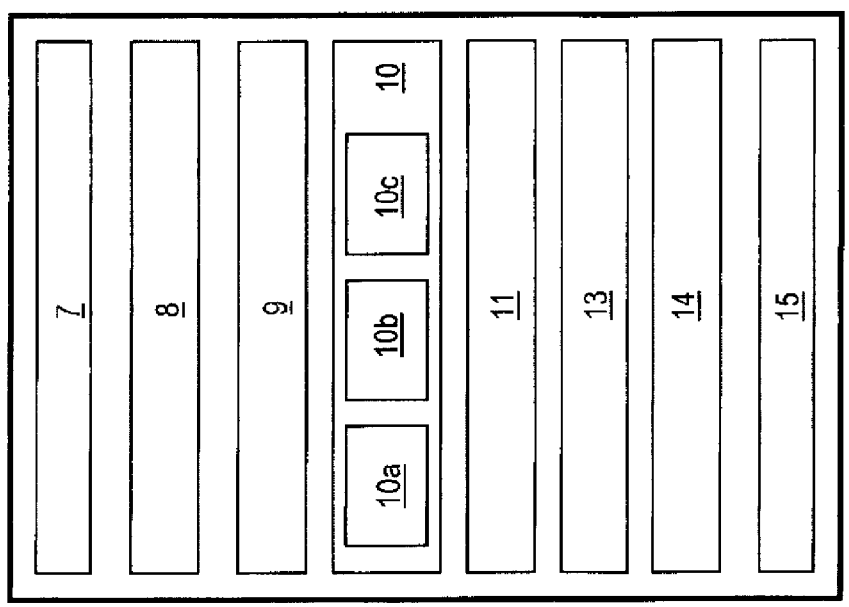
FIG. 2 is a block diagram of the alert apparatus according to the invention.
Figure 2:

With reference to FIG. 2, the receiving means of the alert apparatus 1 comprises receiving antenna means 7 shown schematically in the block diagram of FIG. 2 and used to receive input signals A.

The receiving antenna means 7 comprises one or more antennas that are of known type and are therefore not illustrated in detail.

The receiving means of the alert apparatus 1 further comprises a receiving and decoding unit 8 of the input signals A, which is also shown schematically in the block diagram of FIG. 2.

The receiving and decoding unit 8 is connected to the receiving antenna means 7, so as to receive therefrom the input signals A. Once the input signals A have been received, the receiving and decoding unit 8 decodes the input signals A, for example by demodulation, so as to use the information contained therein, such as the information on the geographical coordinates or the parameters required to determine the position of the alert apparatus 1 in space.

The alert apparatus 1 further comprises, a storage unit 9, shown schematically in the block diagram of FIG. 2, that is suitable for storing and saving data such as the information contained inside the input signals A, for use of the information after reception.

The storage unit 9 is then connected to the receiving and decoding unit 8 so as to be able to receive the information contained in the input signals A and decoded thereby.

The storage unit 9 further contains, the features of the aircraft, space vehicle or flying object in general that moves through the atmosphere or the space in which the alert apparatus 1 is mounted, which are used, as will be explained better below, to determine the extent and the features of the hazard space 2 in functions of parameters such as, for example, mass, overall dimensions, materials that make up the body of the aircraft, space vehicle or flying object in general that moves through the atmosphere or the space and ballistic coefficients.

Alternatively, the storage unit 9 can contain mathematical models relating to the fragmentation features that are specific to each type of aircraft, space vehicle or flying object in general that moves through the atmosphere or the space in which the alert apparatus 1 is originally located.

The alert apparatus 1 further comprises, sensor means 10 arranged for detecting a plurality of data necessary for generating a suitable alert message that is useful for the safety of things or people in flight or on the Earth's surface 20 to be sent to the interface units.

The sensor means 10 is connected to the storage unit 9 so as to gather and keep the detected data.

The sensor means 10 comprises first sensor means 10a arranged for detecting the state of the atmosphere surrounding the alert apparatus 1 after the occurrence of a explosion and/or ablation.

The state of the atmosphere is measured by a plurality of parameters that contribute to defining the features thereof.

The main parameters that characterise the atmosphere are temperature, pressure and density.

The first sensor means 10a is thus suitable for defining the features of the atmosphere inside which the alert apparatus 1 is located when an explosion and/or ablation of the body of the aircraft, of the space vehicle or of the flying object in general that moves through the atmosphere or the space occurs in which the alert apparatus 1 was previously placed or when reentry conditions occur.

For example, the first sensor means 10a may comprise a pressure sensor and a temperature sensor, owing to which, through equations of known type, it is possible to obtain the density.

The first sensor means 10a, by detecting the characteristic parameters of the atmosphere, in particular pressure and temperature, can also be used for detecting an explosion and/or ablation of the body of the aircraft, space vehicle or flying object in general that moves through the atmosphere or the space on which the alert apparatus 1 is mounted.

The first sensor means 10a, by detecting one parameter or a combination of the parameters that characterise the atmosphere, can also be used to activate the alert apparatus 1, which, in the absence of determined pressure and temperature conditions, can be put on standby or be switched off.

Alternatively, the sensor means 10 may comprise one or more acceleration sensors, which are suitable for detecting a explosion and/or ablation characterised by a set acceleration condition, for example a sudden or high-value acceleration or a set deceleration condition. Also the acceleration sensor or acceleration sensors, once an acceleration or deceleration condition has been detected that is traceable to an explosion and/or ablation and/or to a reentry into the atmosphere in the case of a space vehicle or space object can be used to activate the alert apparatus 1.

Still alternatively, the occurrence of an explosion and/or ablation can be detected by the alert apparatus 1 by means of one or more electrical, mechanical or electromechanical connections of said sensor means 10, such as, for example, an electric wire connected directly or by further sensor means 10b to parts of the body of the aircraft, space vehicle or flying object in general that moves through the atmosphere or the space subjected first in terms of time and resistance to the explosion and/or ablation, such parts may be the parts of the external surface of the body, which are identifiable, for example, in solar panels, where present.

Also the further sensor means 10b, once an explosion and/or ablation condition is detected, can be used to activate the alert apparatus 1.

Alternatively, the alert apparatus 1 can be activated manually by the crew of the aircraft, of the space vehicle or of the flying object in general that moves through the atmosphere or the space in which the alert apparatus 1 is originally mounted, or remotely, in particular in the case of unmanned space vehicles.

For example, the alert apparatus 1 can be activated by an activation signal C sent by the aircraft 4, by the ground station 5 or by the end user 6.

Also, the alert apparatus 1 can be activated by the space vehicle 3 following an activation signal C coming from the aircraft 4, from the ground station 5, from the end user 6 or from a further ground station 17.

Unlike the aircraft 4, the ground station 5 and the end user 6, the further ground station 17 does not dialogue directly with the alert apparatus 1, but dialogues therewith only through the space vehicle 3, for example because it is too far from the alert apparatus 1.

The sensor means 10 further comprises second sensor means 10c, arranged for detecting a position of the alert apparatus 1 with respect to a tern of Cartesian reference axes in space starting from a known initial position that is acquired, for example, from a satellite constellation or from a positioning system inside the body of the aircraft, of the space vehicle or of the flying object in general on which the alert apparatus 1 is originally mounted. Starting from the known initial position, the second sensor means 10c supplies the information to a processing unit 11 to update in real time the position of the alert apparatus 1 in space according to the speeds, accelerations and angular variations to which it is subjected.

In particular, the second sensor means 10e may comprise one or more acceleration sensors, which can be the same sensors that are used to detect an explosion and/or ablation, and one or more gyroscopes.

The combination of the signals detected by the second sensor means 10c with the information relating to a known initial position carried by the input signals A coming from the positioning system inside the body of the aircraft, space vehicle or flying object in general or from an artificial constellation of satellites including the GPS, GALILEO or Iridium systems enables the alert apparatus 1 to determine its position with respect to a tern of reference axes.

Alternatively, the position of the alert apparatus 1 in space is established outside the space, i.e. without the use of the second sensor means 10c, for example by using an artificial constellation of satellites including, for example, the GPS, GALILEO or Iridium systems.

The alert apparatus 1 further comprises, a processing unit 11, shown schematically in the block diagram of FIG. 2, that is suitable for gathering and processing data coming from the sensor means 10 to which it is connected.

The processing unit 11 comprises electronic devices of known type, such as a microprocessor, memories and other electronic and circuitry components that are indispensable to the operation of the processing unit 11, such as, for example, oscillators or real time clocks or analog/digital converters or the like that are not shown.

The processing unit 11 is further connected to the storage unit 9.

The processing unit 11 gathers and processes the information on the atmospheric parameters and on the position of the alert apparatus 1 to determine the characteristic parameters of the hazard space 2 inside which the debris and the like are distributed that are generated following an explosion and/or ablation of the body of a aircraft, space vehicle or flying object in general that moves through the atmosphere or the space on which the alert apparatus 1 according to the invention is mounted.

Such characteristic parameters of the hazard space 2 comprise, for example, position, altitude, direction and speed of the hazard space 2 and are also influenced by the speed components of the aircraft, of the space vehicle or of the flying object in general that moves through the atmosphere or the space on which the alert apparatus 1 is mounted, which, in turn, depend also on the presence of atmospheric currents such as the jet streams, and in the case of a space vehicle or of a space object in general, also on the angle of reentry into the atmosphere.

The processing unit 11, by processing both the characteristic parameters of the hazard space 2, and the data stored in the storage unit 9 determines, in particular, the extent and the dynamics of the hazard space 2 of the aircraft, of the space vehicle or of the flying object in general that moves through the atmosphere or the space on which the alert apparatus 1 is mounted.

The result of the computation of the processing unit 11 is then correlated with the geographical position of the alert apparatus 1.

Following the computation, the processing unit 11 obtains a geometrical representation with one or several dimensions, for example a four-dimensional representation, of the alert space 2, having as dimensional variables at least a height from the ground (altitude), a time and two dimensions indicating the movement on the Earth's surface, such as a latitude and a longitude.

Figure 3:
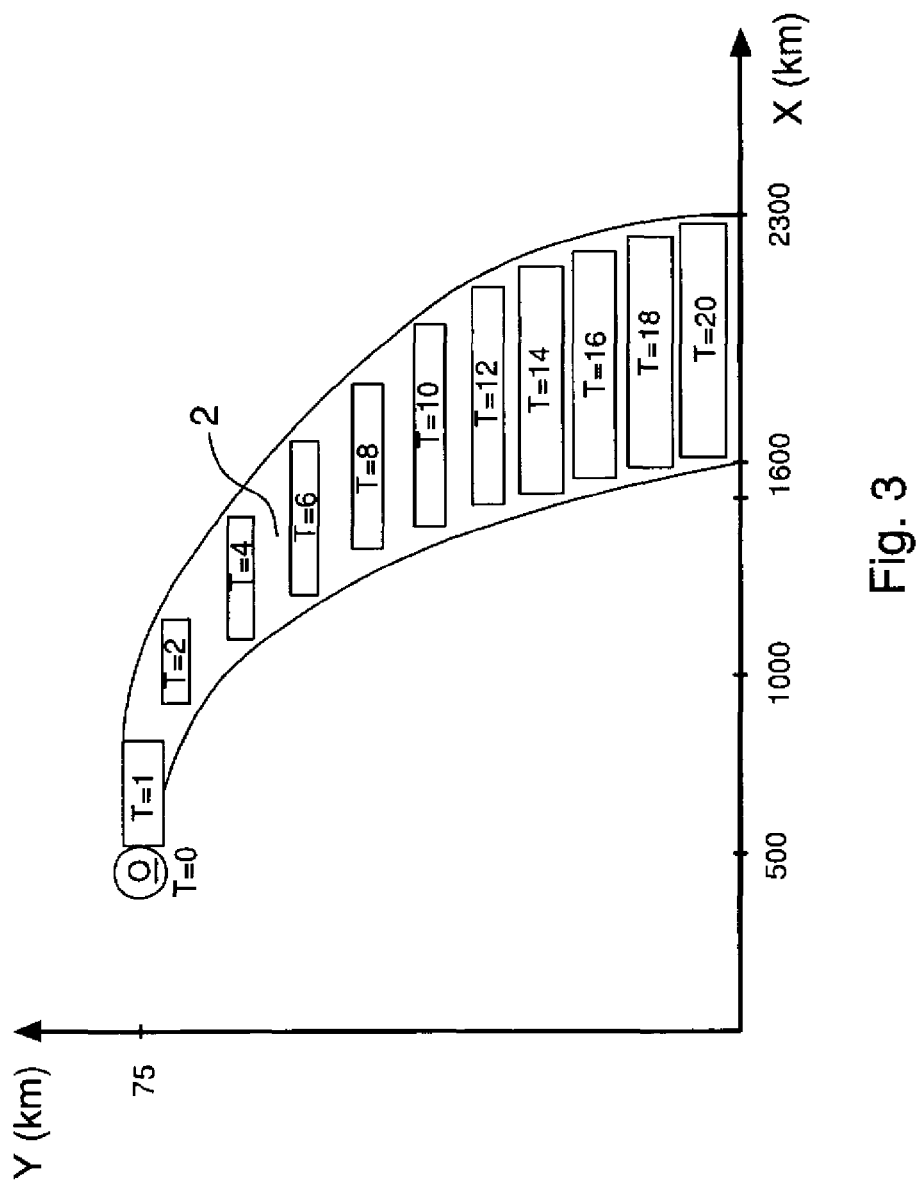
FIG. 3 is a graphic of a three-dimensional projection of the hazard space.

In FIG. 3 is shown a projection of said geometrical representation, said projection simulating the evolution of the shift of the hazard space 2 with the passing of time from the moment of creation thereof to the moment in which it impacts the Earth's surface 20.

The passing of time is represented generically in FIG. 3 by rectangles positioned inside hazard space 2. In particular, the time is indicated with T and the numbers inside the rectangles can indicate the minutes or, generically, instants of time following the moment of the explosion and/or ablation that gave rise to the release of debris and the like.

In particular in FIG. 3 a three-dimensional projection is shown relating to a presumable hazard space 2 generated following an explosion and/or ablation, or following an impact between an aircraft, a space vehicle or a flying object in general that moves through the atmosphere or the space and a piece of debris occurring in an impact zone O.

In FIG. 3, on the X axis the Earth's surface is shown and thus a shift thereof, whereas on the Y axis the height is shown with respect to the Earth's surface, i.e. an altitude.

The hazard space 2, enclosed by the three-dimensional geometrical representation of FIG. 3, defines an area inside which objects and/or persons in flight and/or on the Earth's surface 20 can be hit by one or more pieces of debris.

FIG. 3 shows one of the possible projections of the hazard space 2 and is thus attached only by way of example.

The processing unit 11, once all the data have been gathered and the geometrical representation has been created, adapts the information gathered to a communication protocol, creating alert/hazard signals that are able to be decoded by a plurality of users.

In order to transmit the aforesaid alert signal, still with reference to FIG. 2, the transmitting means comprises an encoding and transmitting unit 13 of the alert signals, which is also shown schematically in the block diagram of FIG. 2.

Once the alert signals have been received by the processing unit 11, the encoding and transmitting unit 13 encodes the alert signals, for example by modulation, generating corresponding output signals B that carry an alert message to the interface units.

The encoding and transmitting unit 13 is connected not only to the processing unit 11 but also to transmission antenna means 14 of the transmitting means of the alert apparatus 1, so as to send thereto the output signals B encoded for transmitting to the interface units.

The transmission antenna means 14 is shown schematically in the block diagram of FIG. 2 and is used to transmit output signals B.

The transmission antenna means 14 comprises one or several antennas of known type that are not therefore illustrated in detail.

The information carried by the output signals B may comprise the position of the alert apparatus 1 in space with the passing of time and the presumed impact position of the debris and the like distributed in the hazard space 2 with the Earth's surface 20.

Different information is processed for each type of interface unit that receives the output signals B.

For example, when the interface unit is a space vehicle 3 or an aircraft 4 in flight, the information contained in the output signal B can be displayed on a display device such as a display of a navigation system and can be processed by processing means of the space vehicle 3 or of the aircraft 4 to determine the time remaining to the impact and a recommended manoeuvre to avoid entering the alert space 2, if the space vehicle 3 or the aircraft 4 is not inside the alert space 2, or to take the space vehicle 3 or the aircraft 4 outside the alert space 2 if the space vehicle 3 or the aircraft 4 is already inside the alert space 2, depending on the current and envisaged flight parameters of the space vehicle 3 or of the aircraft 4.

When the interface unit is a ground station 5 or an end user 6, the information contained in the output signal B can also be displayed on a display device and can be processed by processing means of the ground station 5 to determine the time remaining to the impact and the presumed impact position on the basis of the data received, for example the geometrical representation created by the processing unit 11.

Whilst the output signals B are being sent they may encounter plasma phenomena that prevent or attenuate transmission.

In order to lessen the plasma phenomena that may be generated, various solutions may be devised to counter this phenomenon.

The alert apparatus 1 can provide different ways of transmitting the output signals B.

For example, the output signals B can be sent omnidirectionally and/or directionally towards or away from the Earth's surface, then towards an end user 6, a ground station 5, an aircraft 4 or a space vehicle 3 at the same time.

In addition, in order to minimise interference with the plasma and increase the probability of said output signals B being broadcast, it is possible to transmit the output signals B in a first step away from the Earth's surface, i.e. towards a space vehicle 3, such as a constellation of satellites, which then directs the output signals B to the Earth's surface, and, in a second step, when the alert apparatus 1 has completed part of the descent to the Earth's surface 20, towards the Earth's surface, i.e. towards an end user 6, a ground station 5 or an aircraft 4.

The output signals B can be transmitted continuously from the start moment until the alert apparatus 1 impacts with the Earth's surface 20.

The alert apparatus 1 further comprises a supply system 15, shown schematically in the block diagram of FIG. 2.

The supply system 15 can comprise rechargeable or non-rechargeable batteries, and devices for converting and storing energy that are suitable for converting mechanical or thermal energy into electric power and are suitable for storing the latter. These energy-collecting devices can be used for recharging batteries or for running the alert apparatus 1 independently. The supply of the supply system 15 can thus be detached from the need for a mains power supply owing to the batteries or the energy-collecting devices.

The supply system 15 can be inside the alert apparatus 1.

Alternatively, or in addition, the alert apparatus 1 can also be supplied by external supply systems found in the aircraft, in the space vehicle or in the flying object in general that moves through the atmosphere or the space in which it is mounted.

All the electrical components of the alert apparatus 1 are connected directly or indirectly to the supply system 15.

The operation of the alert apparatus 1 will be disclosed below.

The alert apparatus 1 is mounted inside or outside the body of a aircraft, of a space vehicle or of a flying object in general that moves through the atmosphere or the space.

Once mounted, the alert apparatus 1 can be put on standby status in which the electronic components of the alert apparatus 1 do not operate but are ready to switch from non-operating mode to operating mode.

Alternatively, the alert apparatus 1 can be placed in switched-off status during which all the electronic components of the alert apparatus 1 are switched off.

In the storage unit 9 the actual features of aircraft, of the space vehicle or of the flying object in general that moves through the atmosphere or the space in which the alert apparatus 1 is mounted are stored, i.e., for example, the mass, the dimensions, the features of the constituent materials and ballistic coefficients, that are the parameters that are useful for determining the extent of a possible hazard space.

Alternatively, in the storage unit 9 the mathematical models are stored relating to the specific fragmentation features for each type of aircraft, space vehicle or flying object in general that moves through the atmosphere or the space in which the alert apparatus 1 is located.

The alert apparatus 1 can be activated automatically when the first sensor means 10*a* or the further sensor means 10*b* detect an explosion and/or ablation (for example, when a preset temperature has been reached, a temperature sensor can close the supply circuit of the supply system 15), or can be activated manually by the crew of the aircraft, of the space vehicle or of the flying object in general that moves through the atmosphere or the space on which the alert apparatus 1 is mounted during any step preceding the flight or during any flight step (for example before the reentry into the atmosphere) or can be activated remotely.

When conditions occur of rate of deceleration and/or heat and/or pressure and/or mechanical variations that are typical of an explosion and/or ablation and/or of reentry in the atmosphere of the body on which the alert apparatus 1 is originally mounted, the latter switches on and the receiving antenna means 7, the receiving and decoding unit 8, the storage unit 9, the sensor means 10, and the processing unit 11 are activated that are intended to determine the position and the features of the descent profile and the extent and dynamics of the hazard space 2 generated by the explosion and/or ablation.

In fact, once the alert apparatus 1 has entered the activation step, the processing unit 11 gathers all the data coming from the storage unit 9, from the sensor means 10 and from the interface units and processes the data to determine the extent and the dynamics of the hazard space 2 that is typical of the aircraft, the space vehicle, the flying object in general that moves through the atmosphere or the space on which the alert apparatus 1 is mounted.

The result is then correlated with the geographical position determined according to the reference terrestrial globe model, thus obtaining a geometrical representation like that in FIG. 3 that illustrates a three-dimensional projection of a multidimensional geometrical representation of the hazard space 2 inside which objects and/or persons in flight and on the Earth's surface can be hit by one or more pieces of debris and the like.

Depending on the three-dimensional projection of the hazard space 2 enclosed by the geometrical representation, there are defined a presumable volume inside which objects and/or persons in flight can be hit by one or more pieces of debris and a presumable impact area with the ground inside which objects and/or persons on the Earth's surface 20 can be hit by one or more pieces of debris of the hazard space 2 when they impact the ground.

The volume and the area of impact of the hazard area with the Earth's surface are estimated through conservative approximation.

Once the transmission mode of each of the output signals B has been established the information obtained by the processing unit 11 is adapted to a communication protocol, which is sent to the encoding and transmitting unit 13 to be able to be encoded and transmitted to the interface units as an output signal B omnidirectionally and/or directionally, depending on the type of transmission antenna means 14 mounted in the alert apparatus 1 via ether through the transmission antenna means 14.

In this manner all the users can be reached directly and/or indirectly who are inside or may enter the hazard space 2 during the entire period of descent of the debris and the like.

The output signal B carries an alert/hazard message that is able to be decoded and possibly displayed by the users concerned.

These users may comprise a crew of an aircraft or space vehicle having a route intersecting with the hazard space 2 or one or more users on the Earth's surface 20 and they are alerted so as to activate the respective emergency procedures.

In order to increase as much as possible the number of users to which the output signal B is sent and increase the time margins available, the alert apparatus 1 can send the same alert message also to an artificial satellite constellation on a predefined channel such as the SAR (search and rescue) channel.

The alert apparatus 1 can transmit the message in real time during the entire descent of the hazard space 2 in the atmosphere in order to increase the probability of the message being received by the users.

The interface units can be provided with suitable processors for decoding the alert message.

When the alert message reaches a ground station 5 or a further ground station 17 this can be reprocessed and retransmitted to further end users 16 through various communication means, such as, for example SMS, Internet, data transmission networks such as data-link, or can be retransmitted away form the Earth's surface 20 to reach, for example, a crew in flight that has not yet received the alert message.

Depending on the features of the end user 6 or of the further end user 16 that receives the message and on the processor used, the latter will develop and supply specific information and different emergency procedures will be activated.

For example, if the message reaches a space vehicle 3 or an aircraft 4 in flight, the information contained in the output signal B can be displayed on a display device, such as a display of a navigation system, and can be processed by the processing means of the space vehicle 3 or of the aircraft 4 to determine the time remaining to the impact and a recommended manoeuvre to avoid entering the alert space 2, if the space vehicle 3 or the aircraft 4 is not inside the alert space 2, or for exiting the alert space 2 if the space vehicle 3 or the aircraft 4 is already inside the alert space 2, depending on the current and envisaged flight parameters of the space vehicle 3 or of the aircraft 4.

Consequently, in this case the pilot of the space vehicle 3 or of the aircraft 4 can perform these manoeuvres obtained according to the information carried by the output signal B.

If the message reaches a ground station 5 or an end user 6, the information contained in the output signal B can also be displayed on a display device and can be processed by processing means of the ground station 5 to determine the time remaining to the impact and the presumed impact position on the basis of geometrical representation created by the processing unit 11.

In this case, the emergency procedures to be activated consist, for example, of making safe through appropriate procedures possible sensitive installations such as electric power stations, chemical plants on-land or off-shore drilling rigs and/or ships located in the area of presumed impact between the hazard space 2 and the Earth's surface 20 or in finding a safe shelter for the end users 6 or the further end users 16 who are also located in the area of presumable impact between the hazard space 2 and the Earth's surface 20.

The alert apparatus 1 can also be used as part of civil defence. In fact, the assigned interface unit, once the alert message contained in the output signal B is received, can retransmit the alert message to other bodies or to the further end users 16 that are not directly reached by the alert apparatus 1.

Owing to the alert apparatus 1 according to the invention, information on a hazard space can be sent directly to the end users and also to all the vehicles on the Earth's surface and in flight, ensuring sufficient time for the former to take shelter or activate procedures for making safe sensitive plants and for the latter to be able to exit the hazard space, not enter it, or land.

For example, the time of descent in the atmosphere of the fragments of a vehicle during reentry step form a pressure altitude of about 75 km until impact with the Earth, according to studies already published, is about 20 minutes. It has been further elucidated that from an altitude at the start of the transmission of the output signals B of about 100 km the debris takes about 9.75 minutes to reach a height of about 12 km above the Earth's surface 20, a time that is sufficient to enable emergency procedure to be applied such as, for example, an evasive manoeuvre for the aircraft present.

Further, the alert apparatus 1 according to the invention is able to determine a presumed position of the hazard space 2 with greater precision than prior-art alert apparatuses because the position is constantly updated in function of the actual data on the atmosphere surrounding the alert apparatus 1 after the explosion and/or ablation of the aircraft, of the space vehicle or of the flying object in general on which the alert apparatus 1 was originally located and because the features of the hazard space 2 are determined directly at the hazard space 2. In fact, the alert apparatus 1 is mounted on or inside the aircraft, space vehicle or flying object in general that moves through the atmosphere or the space that gives rise to said hazard space 2, and, when it is detached from the aircraft, from the space vehicle or from the flying object in general that has suffered the explosion and/or ablation, it continues to monitor said hazard space 2 directly from the inside thereof.

Lastly, the alert apparatus 1 is significantly efficient, inasmuch as it is able to ensure cover of the transmission of information on a hazard space even in zones that are not reached directly by the services of air-traffic controllers because it acts independently thereof.

The invention claimed is:

1. Direct broadcast alert apparatus for protection against collisions with debris found in the Earth's atmosphere or in space comprising:
    a containing structure mounted outside or inside a body of an aircraft, of a space vehicle or of a flying object which moves through the atmosphere or the space, in which sensor means are housed that are arranged for checking a release of debris, coming from said body following an explosion and/or ablation thereof, that are dispersed in a hazard space and/or arranged for checking conditions that are referable to said explosion and/or ablation and for detecting features of said hazard space,
    a processing unit, arranged in said containing structure, connected to said sensor means for processing said features in order to determine the extent and the dynamics of said hazard space;
    transceiver means arranged for sending an output signal (B) carrying an alert message on the basis of said extent and said dynamics to a space vehicle and/or to an aircraft having a route intersecting said hazard space, and/or to a ground station and/or to an end user arranged on the Earth's surface at a presumed impact area between said hazard space and the Earth's surface in order to activate respective emergency procedures, said sensor means and said transceiver means being positioned at said hazard space.

2. Apparatus according to claim 1, wherein said sensor means comprises first sensor means arranged for detecting a temperature, a pressure and a density that are distinctive of the atmosphere surrounding said containing structure after said release in order to determine said release, and/or said conditions referable to said explosion and/or ablation and said features of said hazard space.

3. Apparatus according to claim 1, wherein said sensor means comprises an acceleration sensor arranged for determining said release and/or a re-entry phase into the atmosphere of said alert apparatus and/or said conditions referable to said explosion and/or ablation.

4. Apparatus according to claim 1, wherein said sensor means comprises electrical and/or mechanical and/or electromechanical connections connected directly or by further sensor means to parts of said body in order to determine said release and/or said conditions referable to said explosion and/or ablation.

5. Apparatus according to claim 1, wherein said transceiver means comprises receiver means provided with reception antenna means arranged for receiving an input signal coming from a satellite constellation and a receiving and decoding unit arranged for decoding said input signal (A) for obtaining positioning information thereof in the space of said containing structure contained therein.

6. Apparatus according to claim 5, wherein said sensor means comprises second sensor means arranged for detecting a position of said containing structure with respect to a tern of Cartesian axes starting from an initial position acquired by said satellite constellation or by a positioning system inside said alert apparatus.

7. Apparatus according to claim 1, wherein said transceiver means comprises transmitting means provided with an encoding and transmitting unit arranged for encoding said output signal (B) and transmission antenna means arranged for sending said output signal (B) from said hazard space.

8. Apparatus according to claim 5, and further comprising a storage unit that is suitable for storing and saving information contained inside said input signal (A) coming from said satellite constellation, information received from said sensor means and features thereof or defined by mathematical models of said aircraft, of said space vehicle or of said flying object that moves through the atmosphere or space on which said containing structure is originally mounted.

9. Direct broadcast alert method for protection against collisions with debris in the Earth's atmosphere or in space comprising the steps of:
  activating an alert apparatus by sensor means of said alert apparatus, by direct switching on by an operator or by an activation signal (C) sent remotely;
  monitoring by said sensor means of said alert apparatus a body of an aircraft, of a space vehicle or of a flying object that moves through the atmosphere or space on which or in which said alert apparatus is placed to verify a release of debris, coming from said body following an explosion and/or ablation, that are dispersed in a hazard space and/or for verifying conditions referable to said explosion and/or ablation;
  detecting by sensor means features of said hazard space, when said release occurred;
  processing by a processing unit aid features for determining the extent and dynamics of said hazard space;
  sending by transceiver means an output signal (B) carrying an alert message on the basis of said extent and of said dynamics to a space vehicle, and/or to an aircraft having a route intersecting said hazard space and/or to a ground station, and/or to a user on the Earth's surface at a presumed impact area between said hazard space and said Earth's surface in order to activate respective emergency procedures,
  said detecting said features of said hazard space and said sending said output signal (B) being made from the inside of said hazard space.

10. Method according to claim 9, wherein said processing said features comprises obtaining a geometrical representation simulating the evolution of the movement of said hazard space with the passing of time from the moment of said release to the moment wherein said alert apparatus impacts said Earth's surface.

11. Method according to claim 9, wherein said detecting said features comprises detecting a temperature, a pressure and a density that are distinctive of the atmosphere surrounding said alert apparatus in order to determine a possible transmission mode of said output message (B).

12. Method according to claim 9, wherein said processing comprises decoding an input signal (A, C) coming from a satellite constellation for obtaining positioning information thereof in the space of said alert apparatus contained therein and/or commands for said alert apparatus and/or information required for determining said features of said hazard space.

* * * * *